(12) United States Patent
Shah et al.

(10) Patent No.: US 6,441,064 B1
(45) Date of Patent: Aug. 27, 2002

(54) IMIDAZOLE-PHOSPHORIC ACID SALTS AS ACCELERATORS FOR DICYANDIAMIDE IN ONE-COMPONENT EPOXY COMPOSITIONS

(75) Inventors: Dilipkumar Nandlal Shah, Wescosville; William Edward Starner, Nesquehoning, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/703,311

(22) Filed: Nov. 1, 2000

(51) Int. Cl.$^7$ .............................. C08K 3/20; C08L 63/02
(52) U.S. Cl. ..................... 523/421; 528/89; 528/108; 548/335.1
(58) Field of Search ................. 528/89, 108; 548/335.1; 523/421

(56) References Cited

U.S. PATENT DOCUMENTS

| | | |
|---|---|---|
| 3,329,652 A | 7/1967 | Christie et al. |
| 3,356,645 A * | 12/1967 | Warren ........................ 528/108 |
| 3,418,333 A | 12/1968 | Warren |
| 3,631,150 A | 12/1971 | Green ........................ 260/47 |
| 3,632,427 A | 1/1972 | Green ........................ 117/161 |
| 3,755,253 A | 8/1973 | Rice |
| 4,788,076 A | 11/1988 | Weiss ........................ 427/27 |
| 5,508,328 A * | 4/1996 | Olson ........................ 523/445 |
| 5,534,565 A | 7/1996 | Zupancic et al. ........... 523/454 |

FOREIGN PATENT DOCUMENTS

| | | |
|---|---|---|
| JP | 59020371 | 7/1982 |
| JP | 5883023 | 5/1983 |
| JP | 2053777 | 2/1990 |

OTHER PUBLICATIONS

Lee & Neville, *Handbook of Epoxy Resins.*, McGraw–Hill pp. 10–16, 1967.*

T. Kamon, et al. "Curing of Epoxy Resins. VI. Curing of Epoxy Resins with Acid Salts of Imidazoles", Shikizai Kyokaishi (1977), 50 (1), pp. 2–7.

N. Sawa, et al., "Preparation of 1–Benzylimidazoles as Epoxy Resin Hardeners,"Japan Kokai Tokkyo Koho, 6 pp., Chemical Abstratcs 113:78398.

European Search Report, 01125886.0–21–2, dated Mar. 7, 2002.

European Search Report, 01125885.2–1202, dated Mar. 8, 2002.

* cited by examiner

*Primary Examiner*—Robert Dawson
*Assistant Examiner*—D. Aylward
(74) *Attorney, Agent, or Firm*—Michael Leach

(57) ABSTRACT

A heat curable, a one-component epoxy protective or decorative coating or adhesive composition comprising an epoxy resin, dicyandiamide latent heat activated curing agent and an accelerator for the dicyandiamide curing agent characterized in that an imidazole phosphate salt is the accelerator.

14 Claims, No Drawings

IMIDAZOLE-PHOSPHORIC ACID SALTS AS ACCELERATORS FOR DICYANDIAMIDE IN ONE-COMPONENT EPOXY COMPOSITIONS

BACKGROUND OF THE INVENTION

The present invention relates to latent curing agents and accelerators for epoxy resins including water-based compositions, especially one-component water-based epoxy compositions. "Latent" curing agents are those curatives that in a formulated system remain inactive under normal ambient conditions but react readily with epoxy resin at elevated temperatures. "Accelerators" are those materials that accelerate the reaction between epoxy resin and a curing agent. "One component" epoxy compositions are typically a blend of epoxy resin, curing agent and accelerator as well as additives and fillers.

Current one-component water-based epoxy compositions contain dicyandiamide as a latent curing agent dispersed in aqueous epoxy emulsions. These compositions offer excellent shelf life but require very high temperature to cure. Water-soluble accelerators such as imidazoles can be used with dicyandiamide to increase reactivity, however such accelerators adversely affect shelf stability of compositions.

Commercially available latent curing agents offer long shelf stability and good low temperature cure in 100% solids compositions. However, they are not useful in water-based compositions unless a co-solvent is used to dissolve the latent curing agent. The use of solvents increases VOC (volatile organic component) content and adversely affects the shelf stability of the epoxy composition.

There is a need for a water-soluble accelerator for dicyandiamide latent curing agent in heat curable water-based epoxy compositions.

There is a need for a one-component 100% solids epoxy composition which is cured by dicyandiamide and offers a good balance of low-temperature cure and shelf stability.

There is a need for a one-component water based epoxy composition which is cured by dicyandiamide and offers a good balance of low-temperature cure and shelf stability.

U.S. Pat. No. 3,329,652 discloses curing polyepoxides with acid anhydrides using imidazole salts as activators for the acid anhydride.

U.S. Pat. No. 3,356,645 and 3,418,333 disclose curing polyepoxides with imidazole salts.

U.S. Pat. No. 3,746,686 discloses curable epoxy resin compositions comprising a polyepoxide and a salt of a polycarboxylic acid or anhydride and an imidazole.

U.S. Pat. No. 3,755,253 discloses catalyzing the diaminodiphenylsulfone cure of polyepoxides with an imidazole salt.

T. Kamon, et al, "Curing of Epoxy Resins. VI. Curing of Epoxy resins with Acid Salts of Imidazoles", Shikizai Kyokaishi (1977), 50 (1), pp 2–7 discloses the study of the curing of epoxy resins with alkyl carboxylic acid and phosphoric acid salts of some imidazoles.

JP 58083023 describes a latent epoxy hardener prepared by placing 2-hepta-decylimidazoline in water, adding orthophosphoric acid, mixing for 10 minutes, filtering and drying in vacuo. "Epoxy Dispersion In Adhesive Applications", Adhesives Age, May 1995, pages 34–37, discloses the use of 2-methylimidazole and dicyandiamide in water-based epoxy compositions.

SUMMARY OF THE INVENTION

The present invention is directed to imidazole phosphate salts as accelerators for dicyandiamide latent curing agents and their use in one-component heat curable epoxy compositions, especially water-based compositions. The salts are the reaction product of an imidazole and phosphoric acid.

Illustrative of the imidazoles useful for making the accelerators are those compounds of the structure A

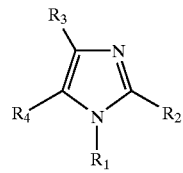

where $R_1$, $R_2$, $R_3$ and $R_4$ are independently hydrogen, a C1–C18 alkyl, a phenyl or a C7–C12 alkylaryl group, these substituent groups optionally containing a functionality such as but not limited to ether, alcohol, amine, nitrile, mercaptan and thiol.

The reaction of these imidazoles with phosphoric acid affords the dihydrogen phosphate salt, or biphosphate, of the following structure B

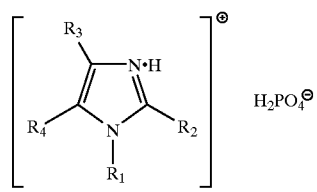

where $R_1$, $R_2$, $R_3$ and $R_4$ are as described above.

The invention provides:

accelerators for dicyandiamide curative in heat cured epoxy compositions.

a water-soluble accelerator for dicyandiamide cured heat curable water-based epoxy compositions.

one-component 100% solids epoxy compositions comprising an imidazole-phosphate salt, dicyandiamide and an epoxy resin which offer a good balance of low-temperature cure and extended shelf stability.

one-component water based epoxy compositions comprising an imidazole-phosphate salt, dicyandiamide and an epoxy resin which offer a good balance of low-temperature cure and shelf stability.

The imidazole phosphate salts are water soluble and accelerate epoxy reactions with dicyandiamide.

DETAILED DESCRIPTION OF THE INVENTION

The invention relates to imidazole (IM) salts of phosphoric acid and their use as accelerators for dicyandiamide in curing epoxy resins. (Phosphoric acid is also known as orthophosphoric acid and is commercially available as 85% phosphoric acid.) While any imidazole that forms a salt with phosphoric acid, which salt is preferably water soluble for water-based compositions, can be suitably used, the preferred imidazoles for use in the present invention are those having the structure A. Salts having structure B are the monobasic salts, or dihydrogen phosphate salts, formed by the reaction of 1 mole of an imidazole with 1 mole of phosphoric acid according to the reaction scheme:

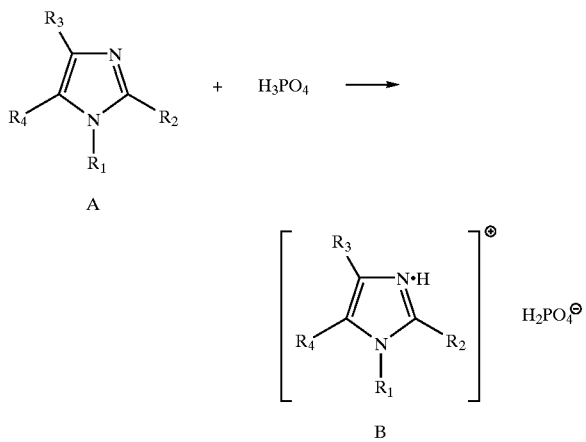

where $R_1$, $R_2$, $R_3$ and $R_4$ are independently hydrogen, a C1–C18 alkyl, preferably a C1 to C3 alkyl, a phenyl or a C7–C12 alkylaryl, preferably C7 to C8 alkylaryl group. Optionally, such alkyl groups may contain a functionality such as but not limited to ether, alcohol, amine, nitrile, mercaptan and thiol.

Suitable alkyl groups include, for example, methyl, ethyl, n- and isopropyl, n-, iso-, sec- and tert-butyl, 2-ethyhexyl, octyl, decyl, dodecyl and heptadecyl.

Suitable alkylaryl groups include tolyl, xylyl and ethylphenyl.

The preferred imidazoles for reacting with phosphoric acid include imidazole, 1-methyl imidazole, also called N-methylimidazole, 2-phenylimidazole and 2-methyl imidazole.

The stoichiometry employed in the synthesis of the phosphate salts can be any combination, e.g., ranging from 0.1 moles to 5.0 moles of imidazole and 0.1 moles to >5.0 moles of phosphoric acid. Generally, the imidazole and the phosphoric acid are reacted in a 0.9 to 1.1 molar ratio, preferably a 0.95 to 1 molar ratio. Typically the commercially available 85% orthophosphoric acid is employed but any concentration can be used in this invention. The reactions can be conducted with or without the use of solvent. The solvents may be but are not limited to water, methanol, ethanol, THF and the like. Any solvent which will dissolve one of the reactants or the product may be used. Any order of addition may be used and the reaction may be conducted at any temperature or pressure desired as they are not critical to making the salt. The preferred method of synthesis is to dissolve the imidazole in methanol and add the orthophosphoric acid slowly to the imidazole solution. The resulting precipitated salt is collected by filtrating, washing with methanol and air drying.

The imidazole/phosphoric acid salts can be used as accelerators for the latent curing agent dicyandiamide in one-component epoxy adhesives, decorative and protective coatings including powder coatings, filament winding, printed circuit board and like epoxy applications. Typically, 0.5 to 10 parts by weight (pbw) dicyandiamide are used in the epoxy composition per 100 pbw epoxy resin, preferably 2 to 6 pbw of dicyandiamide.

The imidazole-phosphate accelerator with the dicyandiamide curing agent is combined with an epoxy resin which is a polyepoxy compound containing more than one 1,2-epoxy groups per molecule. Such epoxies are well known in the epoxy art and are described in Y. Tanaka, "Synthesis and Characteristics of Epoxides", in C. A. May, ed., Epoxy Resins Chemistry and Technology (Marcel Dekker, 1988). Examples include those epoxides disclosed in U.S. Pat. No. 5,599,855 (Col 5/6 to 6/20), which is incorporated by reference. The preferred polyepoxy compounds are the diglycidyl ethers of bisphenol-A, the advanced diglycidyl ethers of bisphenol-A, the diglycidyl ethers of bisphenol-F, and the epoxy novolac resins. Both liquid epoxy resins and solid epoxy resins are suitably used in the one component epoxy compositions. Powder coating compositions would comprise a solid epoxy resin, imidazole phosphate salt and dicyandiamide.

Generally, an effective amount of the imidazole phosphate salts for accelerating the dicyandiamide curing of the epoxy resin is used. As an accelerator for dicyandiamide, 0.5 to 10 parts by weight (pbw) of the phosphate salt would be used per 100 pbw of epoxy resin.

Compositions prepared from phosphoric acid salts of an imidazole, dicyandiamide and epoxy resins can be formulated with a wide variety of ingredients well known to those skilled in the art of coating formulation, including solvents, fillers, pigments, pigment dispersing agents, rheology modifiers, thixotropes, flow and leveling aids, defoamers, etc.

While epoxy compositions comprising 1 to 90 wt % organic solvents or 100% solids can be used, it is preferred the epoxy composition be water-based, i.e., an aqueous epoxy system containing 20 to 80 wt % solids, preferably 50 to 60 wt % solids.

One component epoxy compositions of this invention can be applied as coatings by any number of techniques including spray, brush, roller, paint mitt, and the like. Numerous substrates are suitable for application of coatings of this invention with proper surface preparation, as is well understood in the art. Such substrates include but are not limited to many types of metal, particularly steel and aluminum, as well as concrete.

One component epoxy coating compositions of this invention can be applied and cured at elevated temperatures ranging from about 80° C. to about 240° C., with cure temperatures of 120° C. to 160° C. preferred.

EXAMPLES 1–7

These examples show the preparation of imidazole phosphate salts prepared from the reaction of imidazole (IM), 1-methylimidazole (1MI), 2-methylimidazole (2MI), 2-ethylimidazole (2EI), 2-phenylimidazole (2PI), 2-heptadecylimidazole (2HDI) and 2-ethyl-4-methylimidazole (24EMI) with 85% phosphoric acid in 1:1 molar ratio. The procedure used to prepare these imidazole phosphates was as follows:

To a 250 ml round bottom 3-necked flask equipped with a magnetic stirrer, thermocouple, condenser and dropping funnel was added 100 ml of methanol and the appropriate amount of the desired imidazole, e.g., 17.3 g (0.25 mole) of imidazole (IM). After the dissolution of the imidazole was complete the 85% phosphoric acid was added dropwise over a 15 minute period. When addition was complete the resulting slurry was mixed for 15 minutes. The solid product was isolated by filtration in a Buchner funnel, washed with 50 ml of fresh methanol and dried in air.

The reactant amounts, imidazole phosphate salt yields, their melting points as determined by differential scanning calorimetry (DSC) and pH of a 5% solution of each preparation are shown in Table 1:

TABLE 1

| Example | Imidazole (g) | 85% $H_3PO_4$ (g) | Imidazole Salt (g) | Melting Point (°C.) | pH of 5% soln |
|---|---|---|---|---|---|
| 1 | 17.3 (IM) | 28.8 | 41.5 | 109 | 4.5 |
| 2 | 20.5 (1MI) | 28.8 | 43.9 | 121 | 4.7 |
| 3 | 20.5 (2MI) | 28.8 | 44.0 | 162 | 5.2 |
| 4 | 24.0 (2EI) | 28.8 | 41.7 | 144 | 4.8 |
| 5 | 36.0 (2PI) | 28.8 | 56.5 | 245 | — |
| 6 | 30.6 (2HDI) | 11.5 | 37.0 | 128 | — |
| 7 | 27.5 (24EMI) | 28.8 | 53.6 | 173 | 4.6 |

EXAMPLES 8–14

These examples of 100% solids epoxy systems demonstrate the imidazole phosphate salts as accelerators for dicyandiamide cured epoxy resins. To 6 parts by weight (pbw) of each of the imidazole phosphate salts prepared in Examples 1–7 were added 6 pbw of dicyandiamide (DICY), 1 pbw of fumed silica and 100 pbw of Epon 828 epoxy resin. The resulting mixtures were blended thoroughly for 2 minutes using a high sheer cowls blade mixer. Immediately after preparation the mixtures were examined by DSC to determine the beginning point of exotherm ($T_b$), onset temperature ($T_o$), temperature at maximum exotherm ($T_m$), heat of reaction ($\Delta H$) and glass transition temperature ($T_g$). The DSC analysis was performed using a 2° C./min ramp heat rate on about a 10 mg sample of material. The $T_g$ was obtained by cooling the equipment and test specimen to ambient temperature and rerunning the DSC scan on the sample. The resulting data is shown in Table 2.

TABLE 2

| Example | $T_b$ (°C.) | $T_o$ (°C.) | $T_m$ (°C.) | $\Delta H$ (J/g) | $T_g$ (°C.) |
|---|---|---|---|---|---|
| 8 (IM) | 110 | 126 | 142 | 442 | 153 |
| 9 (1MI) | 114 | 105 | 124 | 469 | 131 |
| 10 (2MI) | 95 | 133 | 140 | 442 | 143 |
| 11 (2EI) | — | 131 | 137 | 447 | 131 |
| 12 (2PI) | — | 145 | 150 | 466 | 148 |
| 13 (2HDI) | — | 119 | 152 | 481 | 127 |
| 14 (24EMI) | 145 | 155 | 166 | 433 | 153 |

EXAMPLES 15–21

These examples of 100% solids epoxy systems demonstrate the imidazole phosphate salts as accelerators for dicyandiamide cured epoxy resins. The mixtures prepared in Examples 8–13 were placed in a constant temperature oven held at 42.5° C. After varying periods of time the mixtures of Examples 8–13 were taken out of the constant temperature oven and analyzed by DSC for remaining heat of reaction ($\Delta H$) following the same procedure as described in Examples 8–14. The results in Table 3 show that the mixtures were stable to epoxy polymerization at 42.5° C. in that they retained nearly all the heat of reaction observed in Examples 8–13.

TABLE 3

| Example | Days @ 42.5° C. | $\Delta H$ | Days @ 22° C. | DH |
|---|---|---|---|---|
| 15 (IM) | 20 | 423 | — | — |
| 16 (1MI) | 11 | 463 | 109 | 459 |
| 17 (2MI) | 20 | 442 | 118 | 408 |
| 18 (2EI) | 20 | 408 | 118 | 421 |
| 19 (2PI) | 24 | 466 | 122 | 400 |
| 20 (2HDI) | 20 | 481 | 118 | 358 |
| 21 (1MI) | 365 | 427 | — | — |

EXAMPLE 22–26

These examples demonstrate the imidazole phosphate salts as water soluble latent accelerators for water borne epoxy emulsions cured with dicyandiamide. The imidazole phosphate salts prepared in Examples 1 and 2 were dissolved in water to make a 50 wt % solution. A mixture was prepared by combining 100 pbw of epoxy emulsion, 3 pbw of dicyandiamide and 6 pbw of 50 wt % aqueous imidazole phosphate solution. The various epoxy emulsions and imidazole phosphate combinations prepared are shown in Table 4. Thin films were cast from each formulation onto glass plates using a 5 mil draw down bar and allowed to dry for 24 hours at ambient temperature. Specimens of the films approximately 10 mg each were then tested by DSC to determine the onset temperature ($T_o$), heat of reaction ($\Delta H$) and glass transition temperature ($T_g$) of the film. The DSC analysis was performed using a 2° C./min ramp heat rate on about a 10 mg sample of material. The $T_g$ was obtained by cooling the equipment and test specimen to ambient temperature and rerunning the DSC scan on the sample. The results are included with the formulations in Table 4.

TABLE 4

| Example | Epoxy Emulsion | $T_o$ (°C.) | $\Delta H$ (J/g) | $T_g$ (°C.) |
|---|---|---|---|---|
| 22 (IM) | Ancarez AR550 | 112 | 257 | 137 |
| 23 (1MI) | Ancarez AR550 | 109 | 240 | 135 |
| 24 (IM) | Epi-Rez 5522 | 109 | 104 | 91 |
| 25 (IM) | Epi-Rez 31515 | 124 | 187 | 107 |
| 26 (IM) | Epi-Rez 3510W60 | 96 | 124 | — |

EXAMPLES 27–29

These examples show imidazole phosphate salts as water soluble latent accelerators of water born epoxy emulsions cured with dicyandiamide. The water born epoxy emulsion formulations prepared in Examples 22, 23 and 24 were stored at 22° C. for 110 days and identified as Examples 27, 28 and 29, respectively. Thin films were then cast from each formulation onto glass plates using a 5 mil draw down bar and allowed to dry for 24 hours at ambient temperature. Specimens of the films approximately 10 mg each were then tested by DSC to determine the onset temperature ($T_o$) and heat of reaction ($\Delta H$) for the film. The DSC analysis was performed using a 2° C./min ramp heat rate on about a 10 mg sample of material. The results are shown in Table 5.

TABLE 5

| Example | Epoxy Emulsion | $T_o$ (°C.) | $\Delta H$ (J/g) |
|---|---|---|---|
| 27 (IM) | Ancarez AR550 | 120 | 268 |
| 28 (1MI) | Ancarez AR550 | 125 | 128 |
| 29 (IM) | Epi-Rez 5522 | 129 | 185 |

Phosphoric acid salts of an imidazole can be used as sole curing agents or as cure accelerators for dicyandiamide in 100% solids as well as in water-based epoxy compositions such as epoxy adhesives, coatings including powder coatings, filament winding, printed circuit board and like applications. These salts do not dissociate until they are exposed to elevated temperatures. Therefore, such materials provide good shelf stability in 100% solids or in water-based one-component epoxy compositions.

STATEMENT OF INDUSTRIAL APPLICATION

The invention provides imidazole phosphate salts as accelerators for dicyandiamide in one-component water based epoxy compositions and 100% solids epoxy compositions.

We claim:

1. In a heat curable one-component epoxy composition comprising an epoxy resin, dicyandiamide latent heat activated curing agent and an imidazole salt composition as an accelerator for the dicyandiamide curing agent, the improvement which comprises an imidazole salt composition consisting essentially of an imidazole dihydrogen phosphate salt as the accelerator.

2. The epoxy composition of claim 1 in which the imidazole dihydrogen phosphate salt has the structure

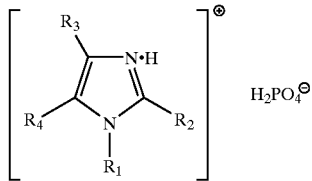

where $R_1$, $R_2$, $R_3$ and $R_4$ are independently hydrogen, a C1–C18 alkyl, a phenyl or a C7–C12 alkylaryl group, the alkyl, phenyl and alkylaryl groups optionally containing an ether, alcohol, amine, nitrile, mercaptan or thiol functionality.

3. The epoxy composition of claim 2 in which $R_1$, $R_2$, $R_3$ and $R_4$ are independently hydrogen, a C1–C3 alkyl, a phenyl or a C7–C8 alkylaryl group.

4. The epoxy composition of claim 1 in which the imidazole dihydrogen phosphate salt is the dihydrogen phosphate salt of imidazole, 1-methylimidazole, 2-phenylimidazole or 2-methylimidazole.

5. The epoxy composition of claim 1 which is a 100% solids epoxy composition.

6. The epoxy composition of claim 5 in which the imidazole dihydrogen phosphate salt is the dihydrogen phosphate salt of 1-methylimidazole.

7. The epoxy composition of claim 5 in which the imidazole dihydrogen phosphate salt is the dihydrogen phosphate salt of 2-methylimidazole.

8. The epoxy composition of claim 1 which is an aqueous epoxy composition.

9. The epoxy composition of claim 8 in which the imidazole dihydrogen phosphate salt has the structure

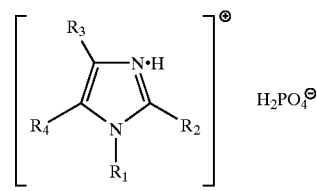

where $R_1$, $R_2$, $R_3$ and $R_4$ are independently hydrogen, a C1–C18 alkyl, a phenyl or a C7–C12 alkylaryl group, the alkyl, phenyl and alkylaryl groups optionally containing an ether, alcohol, amine, nitrile, mercaptan or thiol functionality.

10. The epoxy composition of claim 9 in which $R_1$, $R_2$, $R_3$ and $R_4$ are independently hydrogen, a C1–C3 alkyl, a phenyl or a C7–C8 alkylaryl group.

11. The epoxy composition of claim 8 in which the imidazole dihydrogen phosphate salt is the dihydrogen phosphate salt of imidazole, 1-methylimidazole, 2-phenylimidazole or 2-methylimidazole.

12. The epoxy composition of claim 8 in which the imidazole dihydrogen phosphate salt is the dihydrogen phosphate salt of 1-methylimidazole.

13. The epoxy composition of claim 8 in which the imidazole dihydrogen phosphate salt is the dihydrogen phosphate salt of 2-methyl imidazole.

14. A composition which comprises dicyandiamide curing agent and an imidazole salt composition consisting essentially of the dihydrogen phosphate salt of imidazole, 1-methylimidazole, 2-phenylimidazole or 2-methylimidazole.

* * * * *